United States Patent
Hamilton

(10) Patent No.: US 10,498,443 B2
(45) Date of Patent: Dec. 3, 2019

(54) PORTABLE SOCIAL COMMUNICATION CLIENT

(71) Applicant: Christopher Chad Hamilton, Kirkland, WA (US)

(72) Inventor: Christopher Chad Hamilton, Kirkland, WA (US)

(*) Notice: Subject to any disclaimer, the term of this patent is extended or adjusted under 35 U.S.C. 154(b) by 0 days.

(21) Appl. No.: 15/113,614

(22) PCT Filed: Jan. 22, 2015

(86) PCT No.: PCT/US2015/012439
§ 371 (c)(1),
(2) Date: Jul. 22, 2016

(87) PCT Pub. No.: WO2015/112702
PCT Pub. Date: Jul. 30, 2015

(65) Prior Publication Data
US 2017/0012702 A1  Jan. 12, 2017

Related U.S. Application Data

(63) Continuation of application No. 14/163,729, filed on Jan. 24, 2014, now abandoned.
(Continued)

(51) Int. Cl.
*H04B 10/116* (2013.01)
*H04B 10/114* (2013.01)
(Continued)

(52) U.S. Cl.
CPC ....... *H04B 10/116* (2013.01); *H04B 10/1149* (2013.01); *A61B 5/0017* (2013.01);
(Continued)

(58) Field of Classification Search
CPC .. H04B 10/116; H04B 10/1149; H04B 10/08; H04B 10/11; H04B 10/114; H04B 10/54;
(Continued)

(56) References Cited

U.S. PATENT DOCUMENTS 6,308,227 B1 * 10/2001 Kumar ............... H04L 29/06
709/227
6,720,745 B2 * 4/2004 Lys ................. A61N 5/0616
315/294
(Continued)

FOREIGN PATENT DOCUMENTS

| WO | WO2005111882 | 11/2005 | |
| WO | WO2013/009815 A2 * | 1/2013 | ............ G06Q 10/10 |
| WO | WO2013009815 | 1/2013 | |

OTHER PUBLICATIONS

International Search Report and Written Opinion of the International Searching Authority for corresponding PCT application No. PCT/US2015/012439.

*Primary Examiner* — Kenneth N Vanderpuye
*Assistant Examiner* — Abbas H Alagheband
(74) *Attorney, Agent, or Firm* — Black, McCuskey, Souers & Arbaugh LPA

(57) ABSTRACT

Systems and methods for facilitating social communication are disclosed. A system includes a first portable social client including an encoder configured to associate identity information with an optical signal pattern, and an optical signal transmitter configured to broadcast the optical signal pattern in a series of pulses in a non-visible light spectrum, and a second portable social client including an optical signal receiver configured to receive the optical signal pattern in the non-visible light spectrum, and a decoder configured to access the identity information associated with the optical signal pattern.

10 Claims, 10 Drawing Sheets

Related U.S. Application Data

(60) Provisional application No. 61/930,179, filed on Jan. 22, 2014.

(51) Int. Cl.
  *H04B 10/11* (2013.01)
  *A61B 5/00* (2006.01)
  *A61B 5/11* (2006.01)
  *H04B 10/54* (2013.01)
  *H04N 5/232* (2006.01)
  *E05F 15/43* (2015.01)

(52) U.S. Cl.
  CPC ............. *A61B 5/1112* (2013.01); *E05F 15/43* (2015.01); *H04B 10/11* (2013.01); *H04B 10/54* (2013.01); *H04N 5/232* (2013.01)

(58) Field of Classification Search
  CPC ................................ H04L 9/08; H04L 12/28; G06Q 40/00; G07F 7/10; A61B 5/0017; A61B 5/1112; G11B 11/00; E05F 15/43; H04N 5/232; H04N 5/353; H04N 5/235
  USPC ..................... 398/130, 186, 187, 25
  See application file for complete search history.

(56) References Cited

U.S. PATENT DOCUMENTS

| | | | | |
|---|---|---|---|---|
| 6,922,531 | B2 * | 7/2005 | Smeulders | H04B 10/0799 250/551 |
| 7,415,212 | B2 * | 8/2008 | Matsushita | G06F 3/002 250/206.1 |
| 7,924,759 | B1 * | 4/2011 | LaBella | H04H 20/38 370/312 |
| 8,430,310 | B1 * | 4/2013 | Ho | G06F 21/35 235/382 |
| 9,085,927 | B2 * | 7/2015 | Oshima | H04B 10/11 |
| 9,449,641 | B2 * | 9/2016 | Price | H04N 1/46 |
| 2001/0028227 | A1 * | 10/2001 | Lys | A61N 5/0616 315/317 |
| 2002/0145038 | A1 * | 10/2002 | O'Hagan | G06K 7/0004 235/383 |
| 2002/0178091 | A1 * | 11/2002 | O'Hagan | G06K 7/0004 705/26.1 |
| 2002/0194137 | A1 * | 12/2002 | Park | G06Q 20/10 705/64 |
| 2004/0161246 | A1 * | 8/2004 | Matsushita | G06F 3/002 398/187 |
| 2004/0208641 | A1 * | 10/2004 | Smeulders | H04B 10/0799 398/186 |
| 2004/0229625 | A1 * | 11/2004 | Laroia | H04L 1/1607 455/450 |
| 2004/0267388 | A1 * | 12/2004 | Perdon | G11B 27/005 700/94 |
| 2006/0256070 | A1 * | 11/2006 | Moosavi | H04B 10/1141 345/104 |
| 2007/0061256 | A1 * | 3/2007 | Park | G06Q 20/10 705/40 |
| 2007/0150078 | A1 * | 6/2007 | Tanabe | G08C 17/00 700/33 |
| 2008/0263607 | A1 * | 10/2008 | Gurevich | A61K 9/4858 725/92 |
| 2011/0105041 | A1 * | 5/2011 | Maruyama | G08C 17/02 455/66.1 |
| 2013/0219479 | A1 * | 8/2013 | DeSoto | H04W 12/06 726/6 |
| 2013/0263271 | A1 * | 10/2013 | Xie | H04L 63/145 726/24 |
| 2013/0283397 | A1 * | 10/2013 | Griffin | G06F 21/335 726/28 |
| 2013/0285836 | A1 * | 10/2013 | Proud | G06F 8/65 340/870.02 |
| 2014/0290138 | A1 * | 10/2014 | Oshima | H04B 10/11 49/25 |
| 2015/0146871 | A1 * | 5/2015 | Liu | H04L 9/0852 380/256 |

* cited by examiner

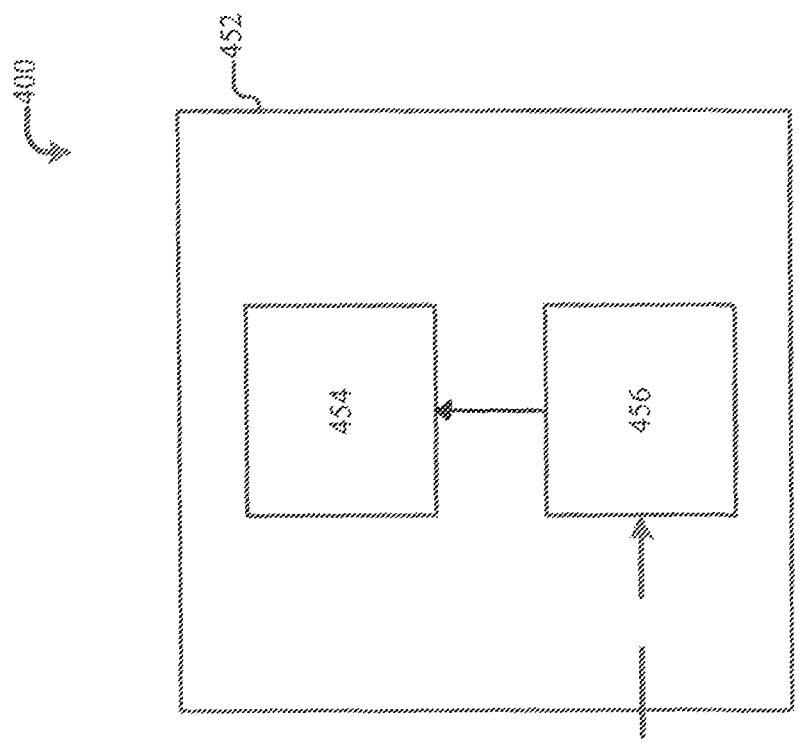
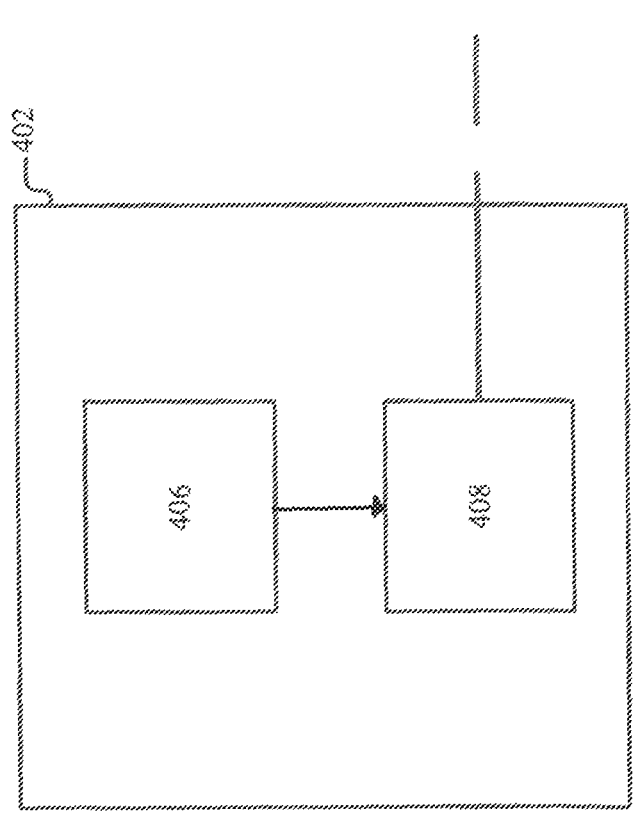
FIG. 4

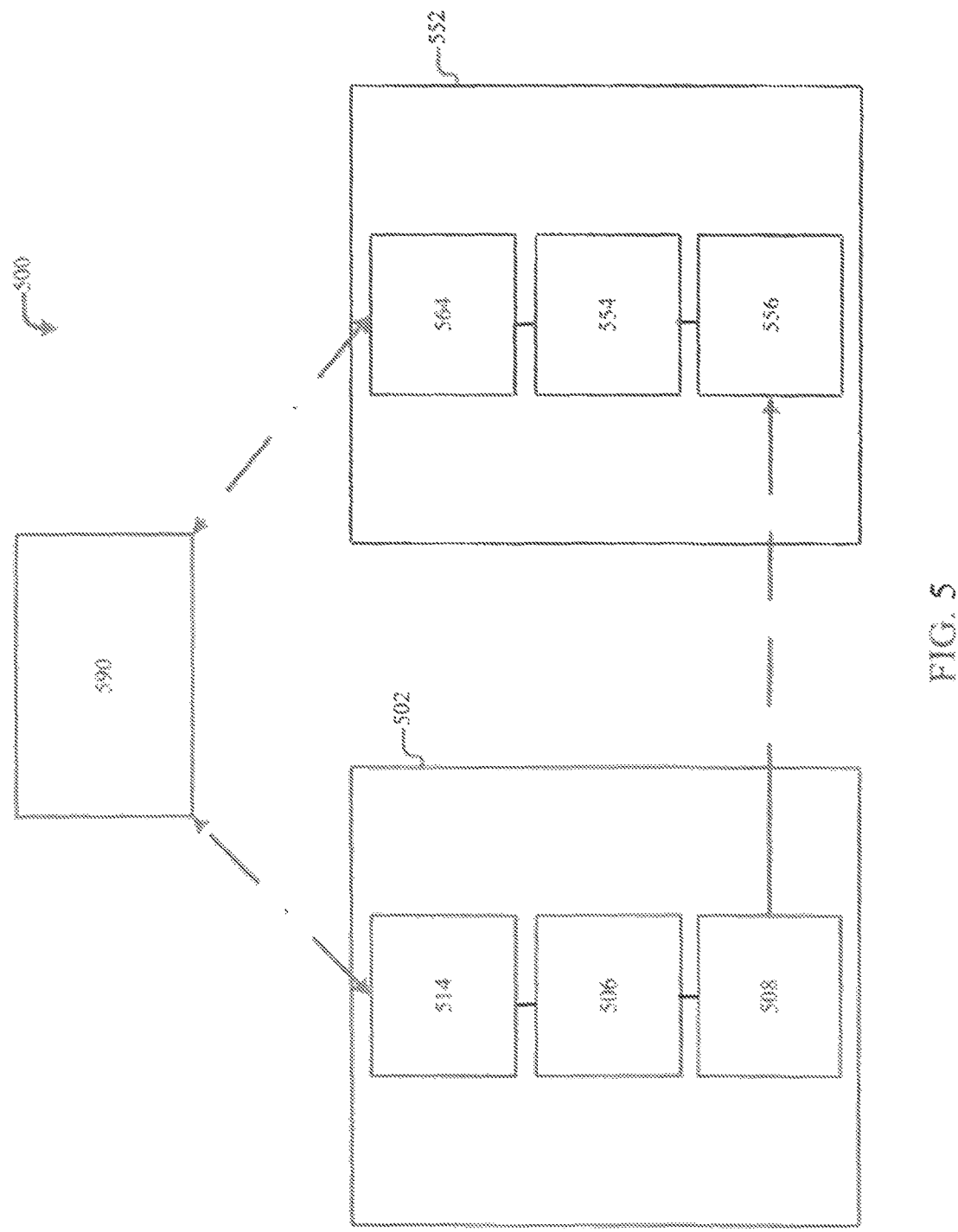

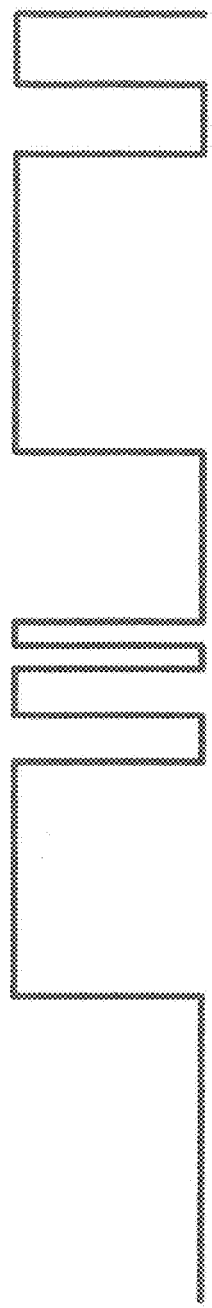
FIG. 6A
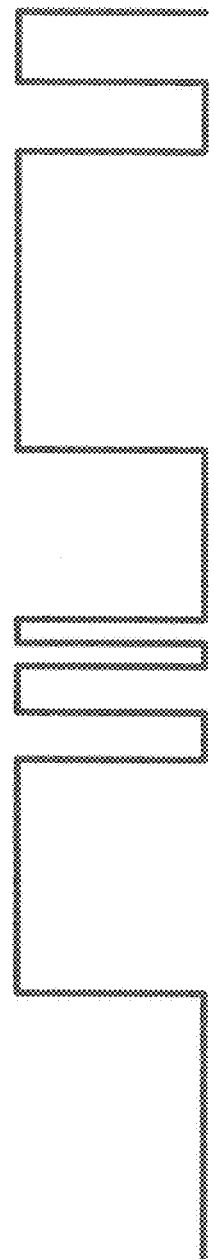
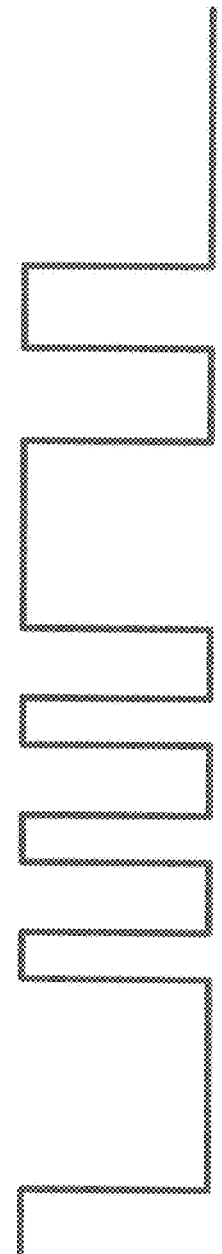
FIG. 6B

PORTABLE SOCIAL COMMUNICATION CLIENT

CROSS-REFERENCE TO RELATED APPLICATIONS

This application is the U.S. National Stage of International Patent Application No. PCT/US2015/012439 filed on Jan. 22, 2015, which claims priority to U.S. patent application Ser. No. 14/163,729, filed on Jan. 24, 2014, which claims priority to U.S. Provisional Patent Application No. 61/930,179, filed on Jan. 22, 2014.

BACKGROUND

This relates in general to portable electronic devices, some of which are wearable or otherwise portable electronic components.

SUMMARY

This relates more specifically to a system including a portable social client, for example a wearable or portable electronic device configured to exchange identity information. The portable social client may have a memory configured to store at least outbound identity information related to a user of the portable social client, an encoder configured to associate at least the outbound identity information from the memory with an outbound optical signal pattern, and an optical signal transmitter configured to broadcast the outbound optical signal pattern.

In at least one embodiment a method for exchanging social information includes providing outbound identity information related to an identity of a user wearing a portable social client, generating an outbound optical signal pattern associated with the outbound identity information, and broadcasting the outbound optical signal pattern associated with the outbound identity information using an optical signal transmitter of the portable social client.

In at least one embodiment, a system includes a first portable social client including an encoder configured to associate identity information with an optical signal pattern, and an optical signal transmitter configured to broadcast the optical signal pattern in a series of pulses in a non-visible light spectrum. The system may further include a second portable social client including an optical signal receiver configured to receive the optical signal pattern in the non-visible light spectrum, and a decoder configured to access the identity information associated with the optical signal pattern.

Various aspects will become apparent to those skilled in the art from the following detailed description and the accompanying drawings.

BRIEF DESCRIPTION OF THE DRAWINGS

FIG. 4 is an illustration of an embodiment of a first portable social client configured to send signals to a second portable social client configured to receive signals.

FIG. 5 is an illustration of an embodiment of a social identity server that communicates with first and second portable social clients.

FIGS. 6A and 6B are illustrations of embodiments of signal pulse patterns.

DETAILED DESCRIPTION

Figure 1:
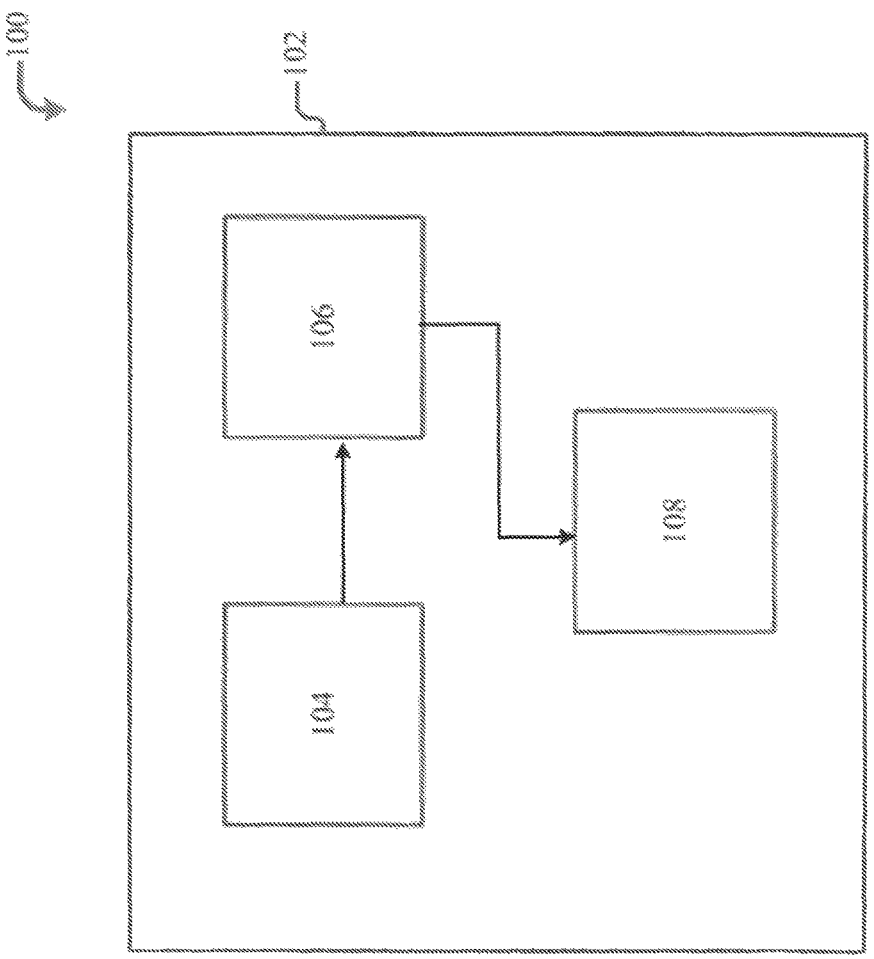
FIG. 1 is an illustration of an embodiment of a portable social client configured to broadcast signals.

In the following description, for purposes of explanation, numerous specific details are set forth in order to provide a thorough understanding. It must be understood that the teachings disclosed may be practiced without these specific details. In some instances, well-known structures and devices are shown in block diagram form in order to facilitate the description. While one or more drawings accompanying this detailed description may or may not be fully discussed in the written description, all aspects from the drawings are wholly incorporated herein, as are any other appendices or supplemental materials. Where materials provided herewith conflict regarding scope or spirit of the description, such conflicting aspects should first be read as alternative or complementary embodiments, and if no such reading is possible, the broader reading shall apply.

Certain embodiments described herein relate to the transmission and reception of identity information using portable and/or wearable social clients.

While the world has become increasingly dependent upon electronic communication and technology, physical presence will remain a major part of relationships. However, when meeting in person, information about others can be difficult to locate or manage. People may forget names, lose business cards or telephone numbers, or may decline to request information out of shyness or uncertainty.

To mitigate this, broadcast techniques can be used to send information automatically between parties. The broadcast techniques may be portable to facilitate use in a variety of environments (e.g., business meeting, industry convention, speed dating event, university class, airport, etc). The broadcast techniques may also be non-disruptive to prevent interruption of personal interactions of senders and receivers or the interactions of others. Finally, the broadcast technique may be secure to prevent unauthorized receipt of sender information.

In this regard, the disclosure herein provides for the use of portable social clients. The portable social clients provide the technical effect of sending and receiving identity information in a semi- or fully-automatic, unobtrusive manner between parties in relative proximity to one another.

The disclosure provides certain embodiments including a system comprising a portable social client. The portable social client includes a memory configured to store at least outbound identity information related to a user of the portable social client, an encoder configured to associate at least the outbound identity information from the memory with an outbound optical signal pattern, and an optical signal transmitter configured to broadcast the outbound optical signal pattern.

In embodiments, the portable social client includes an optical signal receiver of the portable social client, the optical signal receiver is configured to receive an inbound optical signal pattern, and a decoder of the portable social client, the decoder is configured to access inbound identity information associated with the inbound optical signal pattern. In a particular embodiment, the inbound optical signal pattern is further associated with an expiration time after which at least a portion of the inbound identity information is inaccessible by way of the decoder and inbound optical signal pattern.

Further embodiments of the system can include a wireless communication transceiver of the portable social client. In such embodiments, the wireless communication transceiver is configured to communicate with at least a social identity server hosting at least the outbound identity information. In alternative or complementary embodiments, the encoder associates the outbound identity information from the memory with the outbound optical signal pattern by creating the outbound optical signal pattern linking to the outbound identity information on the social identity server. In further alternative or complementary embodiments, the encoder associates the outbound identity information from the memory with the outbound optical signal pattern by partially encoding the outbound identity information from the memory into the outbound optical signal pattern and linking a remainder of the outbound identity information from the memory to the information on the social identity server. In still further alternative or complementary embodiments, interpretation of the outbound optical signal pattern by a remote device facilitates access to the outbound identity information, and wherein the wireless communication transceiver transmits the outbound identity information.

In an embodiment, the encoder associates the outbound identity information from the memory with the outbound optical signal pattern by encoding the outbound identity information from the memory in the outbound optical signal pattern. In another embodiment, the portable social client is wearable.

Embodiments of the system can also include a location module configured to determine a location of the portable social client. In some such embodiments, the outbound optical signal pattern is based at least in part on the location of the portable social client. Embodiments having location based services including an optical signal receiver and a decoder can also provide that the inbound optical signal pattern is interpreted based at least in part on the location of the portable social client.

In an embodiment, the optical signal transmitter broadcasts in one of ultra-violet light and infrared light. In alternative or complementary embodiments, the optical signal transmitter broadcasts in color light.

In still further embodiments, the outbound optical signal pattern is further associated with an expiration time after which at least a portion of the outbound identity information is inaccessible by way of the outbound optical signal pattern.

The technical effect of disclosures herein also provide a method for exchanging social information. The method includes providing outbound identity information related to an identity of a user wearing a portable social client, generating an outbound optical signal pattern associated with the outbound identity information, and broadcasting the outbound optical signal pattern associated with the outbound identity information using an optical signal transmitter of the portable social client.

Further embodiments of the method include receiving an inbound optical signal pattern using an optical signal receiver of the portable social client and interpreting the inbound optical signal pattern to access inbound identity information.

In embodiments, the inbound optical signal pattern includes decoding the inbound optical signal pattern to access inbound identity information on which the inbound optical signal pattern is based. Alternative or complementary embodiments provide that the inbound optical signal pattern includes accessing on a social identity server a server location associated with the inbound optical signal pattern.

In one or more embodiments, the outbound optical signal pattern is broadcast in one of ultra-violet, infrared, or color light. Embodiments of the method can also be realized where the outbound optical signal pattern includes two distinct optical patterns broadcast simultaneously.

In some embodiments, the portable social client is worn by the user.

In further embodiments of the method, the method includes determining a location of the portable social client. In some such embodiments, the outbound optical signal pattern is based at least in part on the location of the portable social client. Alternatively or complementarily, the location is transmitted to a social identity server storing at least a portion of the outbound identity information.

The method can further include, in embodiments, transmitting outbound identity information using a wireless radio transceiver in response to interpretation of the outbound optical signal pattern by a remote device.

Certain embodiments also provide the technical effect of a system comprising first and second social clients. The system includes a first portable social client including an encoder configured to associate identity information with an optical signal pattern, and an optical signal transmitter configured to broadcast the optical signal pattern in a series of pulses in a non-visible light spectrum. The system further includes a second portable social client including an optical signal receiver configured to receive the optical signal pattern in the non-visible light spectrum, and a decoder configured to access the identity information associated with the optical signal pattern.

As used in this application, the terms "component", "system", and "module" are, unless otherwise expressly noted or necessary, intended to refer to a computer-related entity, either hardware, a combination of hardware and software, software, or software in execution. For example, a component or module can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Specific modules are described throughout this disclosure and relied upon in systems and methods herein. Modules are generally capable of one or more of receiving, sending, and/or transforming data electronically. In some instances, handling of information can include energizing or switching related to another module (e.g., powering, controlling, or timing one or more light emitting diodes). Various complex functions can also be performed, such as receiving and processing feedback information, querying a database, and responding based on the feedback and database information. Modules can also be used to transmit, receive, and interpret signals, including signals based on pulses or other arrangements of visible and invisible light.

Generally, communications modules are modules of one or more devices, systems, or subsystems capable of communicating by wired or wireless means with other devices. Such modules are not restricted to communicate exclusively with other devices, and may also communicate or facilitate communication between components or subsystems of which they are a part. Communication modules can use, for example, various proprietary technologies or developed standards (e.g., universal serial bus, Bluetooth, Wi-Fi, infrared, near field communication, radio frequency identification, optical communications, electromagnetic communication, personal area networks, combinations thereof, and others). In embodiments, specific standards or variants may be required to meet constraints such as connectivity, sufficient power, or permit operation. For example, Bluetooth Low Energy (BLE) permits easier device pairing than earlier technologies with regard to subscription and sharing. In another example, a universal serial bus (USB) connected component may require a current (e.g., greater than 0.5 amp, greater than 2 amps, and others) which cannot be provided by early standards of the technology, necessitating a modified or late standard (e.g., USB 2.0, USB 3.0). Communication may also be accomplished using visible or invisible (e.g., ultra-violet or infrared) light as a communication means.

Communication modules can include or be operatively coupled with one or more antennas, or arrays of antennas, for both broadcast and reception. The arrays can be configured to receive not only signals, but include or be coupled with additional hardware or software to determine signal characteristics. In such embodiments, antenna arrays or associated components can determine information related to sending and receiving units. For example, signal strength calculations, power or storage calculations (e.g., voltage, current, battery condition), triangulation (distance, direction, or both), altitude calculation, counting (e.g., of devices in communication), and other information can be discovered and/or provided using communication modules and associated components (including antenna arrays). Further, other information such as environmental conditions, interference, and so forth can be gathered similarly. Light receiving components (e.g., cameras, dedicated photo-sensors/optical sensors, charge-coupled devices, active pixel sensors, et cetera) are used in conjunction with (or as standalone) communication modules.

Modules herein can be flexible, distributed, and/or discontinuous. For example, various sensors, circuits, and devices can be built on flexible materials using boards employing flexibly wired or wireless communication between components, allowing for their arrangement in apparatuses of irregular or changeable shape. In this regard, modules can be integrated into wearable clothing or accessory items, or other elements requiring flexibility for portability or convenience.

Further, modules herein can generally be associated with shared or dedicated storage and processing means for purposes of their function. For example, various hardware, software, or combinations thereof can be utilized to perform energization, de-energization, and timing thereof in relation to provisioning of stimulation. In another example, feedback modules can be operatively coupled with sufficient storage to record feedback collected, and communication modules can in turn be associated with media that is at least readable to facilitate storage of information received and/or transmitted.

As used herein, "devices", "groups of devices", or similar language is intended not (or not only) to refer to one particular device or a heterogeneous group of devices, but can rather refer to a device or group of devices sharing at least some common capability. Devices can be comprised of different hardware, software, and other components. A device as used can be any piece of electronics capable of participating in systems and methods set forth herein. For example, a device can be a cellular telephone (e.g., smart phone) with one or more "apps" (e.g., mobile applications) providing programming that leverages the telephone's existing capabilities.

As with modules generally, devices can be, in some embodiments, wearable elements. As used herein, a "wearable" element or device is one that is integrated into an item of clothing or accessory. For example, a wearable element, structure, or item can be a clothing item with a receiver and sensory stimulation module (and any other necessary components, such as a battery) integrated therein. Examples of clothing can include, but are not limited to, footwear (e.g., shoes, sandals, socks, boots), leg-wear (e.g., pants, shorts, stockings, skirts), underwear (e.g., briefs, panties, thongs, boxers, bras, undershirts), tops (e.g., shirts, blouses, camisoles), outerwear (e.g., jackets, coats, blazers, vests, sweatshirts, robes), headwear (e.g., hats, caps, earmuffs), handwear (e.g., gloves, mittens), and/or other items worn other than accessories. Accessories can include, but are not limited to, jewelry (e.g., bracelet, anklet, ring on any portion of the body, bands, piercings on any portion of the body, necklaces, pendants, charms), glasses, decorative headwear (e.g., crown, tiara, halo), bags or holders (e.g., backpack, fanny pack, purse), functional items (e.g., headphones, mobile devices), belts, costume items, and others.

As used herein, "identity information" relates to the identity of a user. Identity information includes the user's name and contact information (e.g., telephone, e-mail, physical address, and/or others) and may include a photo to assist with recognition. In this regard, identity information can include information similar to that of a business card. Other information, such as profession, business affiliation, interests, relationship status, and others can be included in embodiments where such details concern the parties exchanging identity information. Further, metadata is included in or associated with identity information to aid in its management. Metadata can include, but is not limited to, location constraints on identity data, rules for sharing or interpreting shared identity data, permissions or hierarchies for what data is transmitted to distinct groups of users or individuals, expiration times for a particular identity data broadcast, authentication or handshake information, remote server locations, and others.

Further, identity information or optical signals may be described as "inbound," "outbound," or qualified in other similar manners. In this regard, "inbound" refers to transmissions or data broadcast at another location being received by the receiver at which the transmissions or data are arriving, and "outbound" refers to transmissions or data at their origin, which are being transmitted for receipt at another location.

While various modules or components are shown associated with particular sections, groups, or locations, it is understood that the illustrated embodiments are intended only to show a subset of workable alternatives rather than an exhaustive depiction of all possible arrangements. Further, not all elements need be included, and additional elements may be omitted or added to accommodate additional, remove existing, or combine aspects depicted, without departing from the scope or spirit. Elements described as distributed may be wholly stored or constructed in a single location, and elements shown as static or of known location may be distributed or oriented in fashions not pictured.

FIG. 1 is an illustration of an embodiment of a portable transmitting social client 100 configured to broadcast signals. Portable transmitting social client 100 includes housing 102, memory 104, encoder 106, and optical signal transmitter 108. Housing 102 can be any enclosure or body containing or connecting the elements of transmitting social client 100. In an embodiment, housing 102 is flexible. Housing 102 includes, in an embodiment, construction that renders the other components of transmitting social client 100 resistant to moisture or other contamination. Housing 102 can further include attachment components such as pins, buttons, buckles, hook-and-loop connectors, magnets, et cetera, to facilitate wearability of transmitting social client 100. While embodiments of FIG. 1 and other figures are shown with a housing, it is understood that the elements of transmitting social client 100 are in embodiments distributed and operatively coupled at a distance using wired or wireless communication rather than contained in a single housing.

Memory 104 stores at least a portion of identity information associated with a wearer or user of transmitting social client 100. Memory and techniques related thereto are described further in relation to FIG. 7. Memory 104 can persistently (e.g., user provides information to transmitting social client 100 and information is maintained thereon until further action) or temporarily (e.g., memory 104 stores information received from a server during use but does not maintain information thereafter) store identity information. Other data, such as encoding algorithms or keys, controls for encoder 106 or optical signal transmitter 108, handshake or authentication software, et cetera, can also be stored in memory 104.

Encoder 106 generates an optical signal (e.g., outbound optical signal from a social client having optical signal transmitter 108) based at least in part on the identity information. The optical signal includes information facilitating access to the identity information by a receiver.

After encoder 106 generates the optical signal, optical signal transmitter 108 broadcasts the signal. Broadcasting is conducted by pulsing (e.g., turning on or off at different relative times within the length of the signal) one or more light emitting components of optical signal transmitter 108 to replicate the pattern defined by the optical signal. Light emitting components can include incandescent lamps, fluorescent lamps, light emitting diodes, light emitting plasma, high-intensity discharge lamps, and others. In at least one embodiment, an ultraviolet light emitting component is used to broadcast in ultraviolet (UV) light. In at least another embodiment, an infrared light emitting component is used to broadcast in infrared (IR) light. Other embodiments can employ visible light including color light, or light in other spectrums.

Further, in embodiments multiple light emitting components are included in a single transmitting social client 100 to facilitate the simultaneous broadcast of two or more signals to increase the amount of data transmitted in a length of time. FIG. 6B illustrates such an embodiment, depicting two optical patterns transmitted simultaneously.

Figure 2:
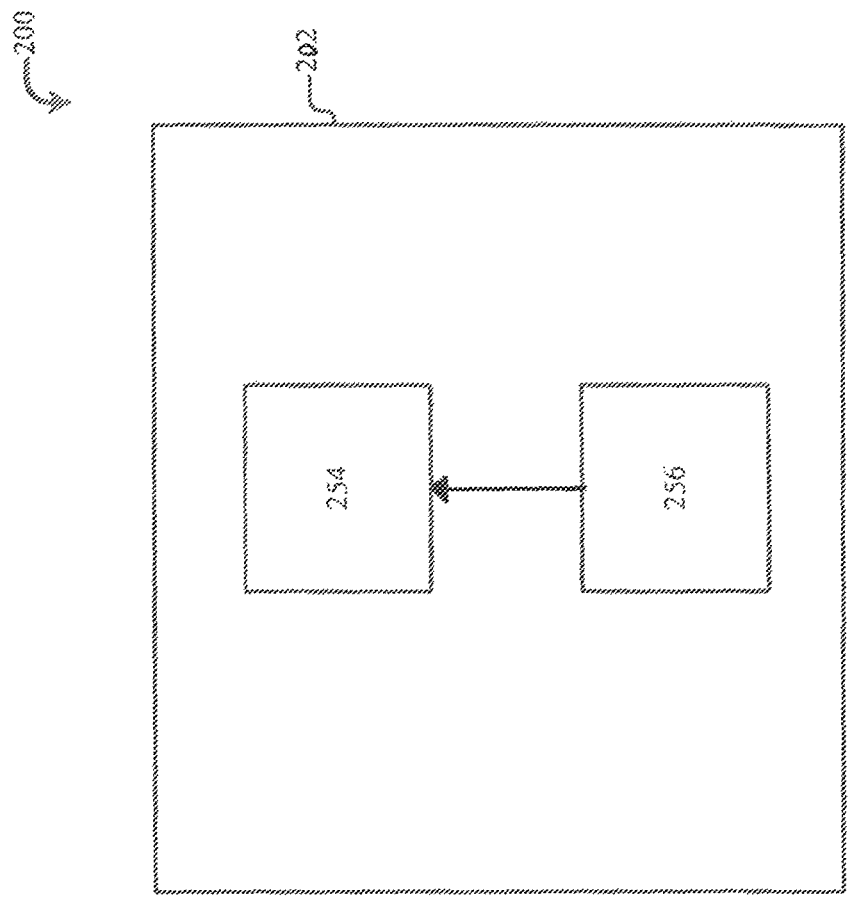
FIG. 2 is an illustration of an embodiment of a portable social client configured to receive signals.

FIG. 2 is an illustration of an embodiment of a portable receiving social client 200 configured to receive signals, and may be complementary to transmitting social client 100. Similar to transmitting social client 100, receiving social client 200 includes housing 202. Housing 202 can be any enclosure or body containing or connecting the elements of receiving social client 200. In an embodiment, housing 202 is flexible. Housing 202 includes, in an embodiment, construction that renders the other components of receiving social client 200 resistant to moisture or other contamination. Housing 202 can further include attachment components such as pins, buttons, buckles, hook-and-loop connectors, magnets, et cetera, to facilitate wearability of receiving social client 200. While embodiments of FIG. 2 and other figures are shown with a housing, it is understood that the elements of receiving social client 200 are in embodiments distributed and operatively coupled at a distance using wired or wireless communication rather than contained in a single housing.

Receiving social client 200 also includes optical signal receiver 256 and decoder 254. While not illustrated, receiving social client 200 also includes memory or other components in embodiments such as those depicted hereafter. Optical signal receiver 256 is configured to detect and receive optical signals and patterns or encoding therein such as described herein. Upon receipt, the optical signal (or a representation thereof) is provided to decoder 254. Decoder 254 interprets the optical signal (or representation thereof) to access identity information associated with the received optical signal.

Accessing the identity information can include decoding the optical signal to discern identity information encoded therein. Accessing identity information alternatively involves receiving a portion of the identity information by decoding the optical signal and receiving a reminder of the identity information through other means. In another alternative, the identity information is accessed through another form of communication (e.g., Bluetooth, Wi-Fi, near field communication) by connecting to another social client or through use of an intermediary server. In embodiments where at least a portion of the identity information is not encoded into the optical signal, the optical signal may include information related to authentication, handshake, protocols, addresses, and/or other metadata or technical information beyond the content sought. Using this additional data, the receiving client may access the identity information.

Because of the possibility for light noise in public, especially where multiple transmitters exist, optical signal receiver 256, decoder 254, and/or other components can be configured to screen for particular conditions prior to interpreting information. For example, thresholds or bands of intensity or amplitude can indicate range or direction, permitting for the arrangement of rules concerning receipt or interpretation. Such rules can permit a multi-faceted approach to be taken, discriminating between "harvested" social data and "handshake" social data. Less-near or direct signals received can be broadly "harvested" to, for example, preserve the names of all people at an after-conference event, while the strongest or most direct signals (which may, for example, indicate a face-to-face interaction) can facilitate further communication between transmitter, receiver, and/or intermediary servers to store phone and e-mail contact information in addition to name. Such examples are provided only to allude to possible configurations, and should not be interpreted as limiting or exhaustive.

Figure 3:
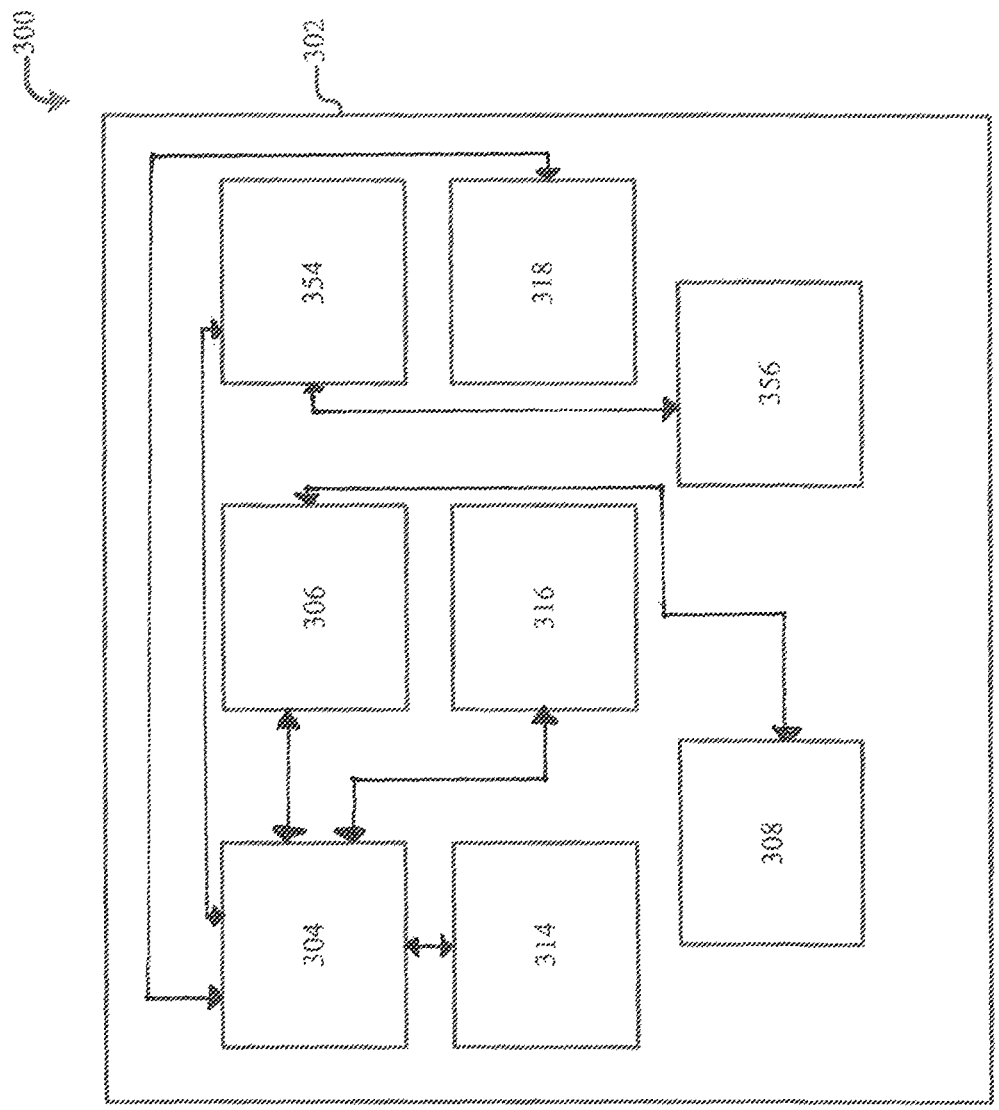
FIG. 3 is an illustration of an embodiment of a portable social client configured to send and receive signals.

FIG. 3 is an illustration of an embodiment of a portable social client 300 configured to send and receive signals. Portable social client 300 includes both an optical signal transmitter 308 and an optical signal receiver 356, as well as associated encoder 306 and decoder 354, and other components. Like other social clients described, portable social client 300 includes a housing 302, which can be flexible or configured according to any arrangement provided with respect to other housings herein. In this regard, portable social client 300 can be carried, worn, or utilized by any person whether sending or receiving optical signals associated with identity information.

Encoder 306 can generate an optical signal associated with identity information according to various techniques, to include contextual factors such as location or others described herein. Portable social client 300 can broadcast signal using encoder 306 and optical signal transmitter 308 in a variety of manners. Broadcasting can be continuous, periodic, on-demand, or according to other broadcast schemes. Continuous broadcasting sends the signal repeatedly. In embodiments employing continuous broadcasting of at least one signal, social clients can be configured to recognize signal breaks to expedite signal recognition based on the beginning and end of one loop. Periodic broadcasting can broadcast according to a repeating or custom schedule for broadcast. On-demand broadcasting can be manual or automatic. In manual embodiments, the user can control the social client to determine when the signal is broadcast. In automatic embodiments, the social client can begin broadcasting in response to location information, detection of other clients, receipt of other signals, and/or on other conditions. In an embodiment, portable social client 300 and/or other clients can broadcast a beacon signal, which is provided to indicate the presence of social clients and initiate broadcasting. On detection of the beacon signal, one or more social clients can begin broadcasting at least one signal.

Portable social client further includes memory 304, which stores identity information as well as computer readable instructions, executable code, or data for use with various other modules of social client 300. Portable social client 300 also includes wireless communication transceiver 314, which can communicate using one or more techniques distinct from that of optical signal transmitter 308 and optical signal receiver 356. For example, wireless communication transceiver 314 can communicate according to Wi-Fi, Bluetooth, near-field communication, or other techniques (e.g., described in relation to FIG. 7). Wireless communication transceiver 314 permits communication with, e.g., other portable social clients, intermediary servers, mobile devices, computers, et cetera, according to wireless networking or communication techniques other than optical signals.

The illustrated embodiment of portable social client 300 also includes location module 316. Location module 316 conducts location assessment social client 300, and in embodiments may complete location assessment of other devices with which social client 300 is in communication. Locations can be determined absolutely (e.g., GPS coordinates) and/or relatively (e.g., direction and distance from other devices with which social client 300 communicates). Various techniques can be utilized to such effect. Near field communication (NFC), device-based triangulation, global positioning systems, motion sensors, gyroscopes, and others can be used to establish location.

Location data from location module 316 can be used to manage identity data and interactions between social client 300 and other social clients. In an embodiment, social client 300 being located in a known area can be used to initiate broadcast of identity information. In alternative or complementary embodiments, the presence of social client 300 in proximity to other social clients can be used to initiate broadcast of identity information. Location data or the presence of one or more disallowed clients can also be used to cease or prevent broadcast of identity information from social client 300. Such aspects can be managed in an ad hoc fashion (e.g., social clients detect service set identifiers being broadcast without connecting) or through central control (e.g., a social identity server or other controller). As can be appreciated, different actions or rules can be tied to different locations.

Location data from location module 316 can also be used to provide context for accessing identity information based on information received. For example, in an embodiment, an optical signal transmitter sends only a short pattern of light pulses, limiting the number of possible signals that can be transmitted. Because the same signal may thus be reused, a location discerned from location module 316 can be used to properly direct a receiving social client to a server location associated not only with the optical signal but also the location. In this manner, embodiments having a limited number of possible optical signal patterns can be used effectively on a large scale where patterns are reused.

Service module 318 provides other functions and services associated with social client 300. Service module 318 can include control software for other modules or components, include coupling capability and input/output functionality, and otherwise enable or enrich capabilities disclosed herein. In an embodiment, service module 318 is used to provide identity information through social client 300 or another device (e.g., smart phone) operatively coupled therewith. Service module 318 can manage multiple sets of identity information associated with a single social client 300 or related group of wearable elements, such as when both temporary and permanent identifiers are employed.

Service module 318 can also provide security and/or authentication features in addition to those provided by other components. For example, service module 318 can manage temporary optical signals by providing time-stamp functionality that disallows social client 300 or devices with which social client 300 is in contact from fully interpreting optical signals, which are expired, and/or deletion of information beyond its expiration time. In managing expiration functionality, service module 318 can apply specified times, durations, locations, events, activities, or statuses that cause optical signals or associated identity information to persist or expire.

In embodiments, service module 318 also oversees pairing of devices using wireless communication transceiver. Because different identity information can be intended for different recipients or classes of recipients, and because different optical signals can be generated, service module 318 can provide appropriate context-specific information to be included in broadcast signals to enable appropriate users to access the appropriate level of information. In this way, event organizers or service administrators can leverage service module 318 to tier levels of access without having to prevent exposure to signals by parties lacking a particular access level.

As suggested above, in various embodiments, service module 318 controls what information is received by a particular recipient and/or what actions can be pursued with the identity information received. Options include signaling an interest to meet later, a request to connect on social networks, a request to communicate electronically, or a request for further information about the sender. The information may be specific to the time, location, event, associations, activities, et cetera, of either a user associated with a transmitting social client or a receiving social client.

Examples of environments for such integration include, but are not limited to, business marketing, professional capabilities, personal hobbies, or personal or private information like relationship status.

In an embodiment, a receiver's access is determined by their own identity information made available. In alternative or complementary embodiments, a transmitter predetermines access to a select group or list. Identity information can also be updated using at least components capable of interacting with service module 318. Updating during the time when identity information is valid allows for a single identity or associated optical signal of a transmitter to represent various facets of professional and personal life to different receivers while providing some privacy protection and pseudo anonymous capabilities.

Service module 318 can also facilitate feedback based on such access or actions. In an embodiment, a receiver is notified of permitted actions and information after receiving an optical signal or establishing other connections (e.g., client-to-client, with intermediary server, and others). In further embodiments, a social client, or hardware associated therewith (e.g., user's cell phone) may prompt completion of permitted actions or viewing of appropriate information.

As suggested, different data can be sent over different media or communication techniques. For example, light signals can be broadcast as public information. In instances where light information is appropriately received (e.g., receiver has decoder with appropriate cryptographic key or permission to access intermediary server), coupling can occur via, e.g., near field communication or Wi-Fi to transfer different or larger portions of information. In an embodiment, public information is broadcast using optical signals, whereas private information is accessed in response to the visual signals but transmitted using a secure alternative technique.

Turning now to FIG. 4, illustrated is an embodiment of a system 400 including first portable social client 402 configured to send signals to second portable social client 452 configured to receive signals. First portable social client 402 includes encoder 406 and optical signal transmitter 408. Encoder 406 generates an optical signal associated with identity information, which is provided to optical signal transmitter 408. Optical signal transmitter 408 then broadcasts the optical signal.

During broadcast of the optical signal by optical signal transmitter 408, optical signal receiver 456 receives the optical signal. The optical signal is then provided to decoder 454, which interprets the optical signal. Based on the interpretation of the optical signal, second portable social client 452 is permitted access to the identity information originating from first portable social client 402.

FIG. 5 is an illustration of an embodiment of a system 500 including a social identity server that communicates with first portable social client 502 and second portable social client 552. First portable social client 502 includes encoder 506 and optical signal transmitter 508. Encoder 506 generates an optical signal associated with identity information, which is provided to optical signal transmitter 508. Optical signal transmitter 508 then broadcasts the optical signal.

During broadcast of the optical signal by optical signal transmitter 508, optical signal receiver 556 receives the optical signal. The optical signal is then provided to decoder 554, which interprets the optical signal. Based on the interpretation of the optical signal, second portable social client 552 is permitted access to the identity information originating from first portable social client 502.

This access is accomplished based at least in part through communication with social identity server 590. First portable social client 502 communicates with social identity server 590 using wireless communication transceiver 514 to provide identity information associated with first portable social client 502 to social identity server 590. After receiving information on how to retrieve identity information from social identity server 590 from an optical signal sent by optical signal transmitter 508 and received by optical receiver 556, second portable social client 552 leverages wireless communication transceiver 564 to access social identity server 590 according to access information (e.g., authentication information, server address, et cetera) identified by decoder 554 based on the optical signal.

In embodiments, in addition to communicating with social identity server 590, wireless communication transceiver 514 and wireless communication transceiver 564 can communicate directly (e.g., transceiver to transceiver) either in response to exchanged optical signals or independent of other component function.

FIGS. 6A and 6B are illustrations of embodiments of signal pulse patterns. FIG. 6A shows a single pattern having various pulses of different lengths, which can be used to encode data. FIG. 6B illustrates two simultaneously broadcast optical signal patterns having pulses of different lengths. Where two signals are broadcast simultaneously, the nature of light used in the broadcast can vary in terms of wavelength/spectrum/color, amplitude/intensity, pattern scheme, et cetera, to facilitate discrimination between signals. While the signals of FIGS. 6A and 6B are shown as binary in nature (e.g., on or off), alternative embodiments can provide for intermediate values (e.g., intensity or amplitude) at a given time. In an embodiment, each pulse is of constant length. In various other embodiments, pulses (or off periods) can be of any length.

In embodiments, multiple transmissions can be encoded in a single optical signal using various band sharing techniques such as those used in other broadcast technologies. For example, schemes analogous to code division multiple access, time division multiple access, et cetera, can be employed in the optical signals.

Where multiple optical signals are used as in FIG. 6B, multiple optical signal transmitters may be employed, or a single transmitter can be utilized to broadcast a variety of distinct pulse types representative of multiple signals.

Figure 7:
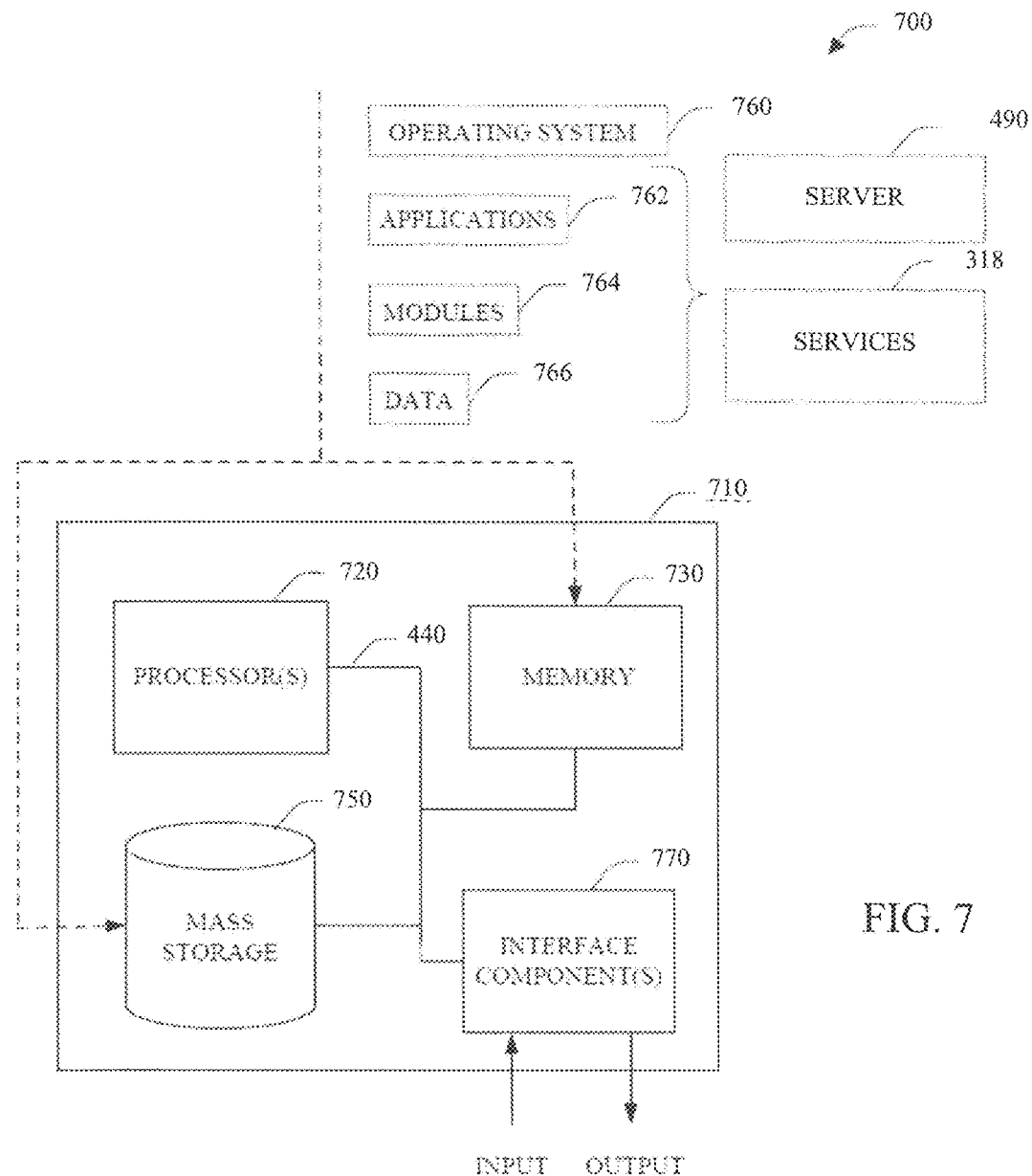
FIG. 7 is an illustration of an embodiment of an example environment, which can be used in conjunction with certain aspects disclosed herein.

In order to provide a context for the claimed subject matter, FIG. 7 as well as the following discussion are intended to provide a brief, general description of a suitable environment in which the subject matter can be implemented. The suitable environment, however, is only an example and is not intended to suggest any limitation as to scope of use or functionality.

While the above disclosed systems and methods can be described in the general context of computer-executable instructions of a program that runs on one or more computers or network hardware, those skilled in the art will recognize that teaching of this disclosure may also be implemented in combination with various alternative hardware, software, modules, et cetera. As suggested earlier, program modules include routines, programs, components, data structures, among other things that perform particular tasks and/or implement particular abstract data types. Moreover, those skilled in the art will appreciate that the above systems and methods can be practiced with various computer system configurations, including single-processor, multi-processor or multi-core processor computer systems, mini-computing devices, mainframe computers, as well as personal computers, hand-held computing devices (e.g., personal digital assistant, portable gaming device, Smartphone, tablet, Wi-Fi device, laptop, phone, among others), microprocessor-based or programmable consumer or industrial electronics, and the like. Some embodiments may also be practiced in distributed computing environments where tasks are performed by remote processing devices that are linked through a communications network. However, some, if not all the subject matter disclosed may be practiced on stand-alone computers. In a distributed computing environment, program modules may be located in one or both of local and remote memory storage devices.

With reference to FIG. 7, illustrated is an example general-purpose computer 710 or computing device (e.g., desktop, laptop, server, hand-held, programmable consumer or industrial electronics, set-top box, game system, et cetera). The computer 710 includes one or more processor(s) 720, memory 730, system bus 740, mass storage 750, and one or more interface components 770. The system bus 740 communicatively couples at least the above system components. However, it is to be appreciated that in its simplest form the computer 710 can include one or more processors 720 coupled to memory 730 that execute various computer executable actions, instructions, and or components stored in memory 730.

The processor(s) 720 can be implemented with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any processor, controller, microcontroller, or state machine. The processor(s) 720 may also be implemented as a combination of computing devices, for example a combination of a DSP and a microprocessor, a plurality of microprocessors, multi-core processors, one or more microprocessors in conjunction with a DSP core, or any other such configuration.

The computer 710 can include or otherwise interact with a variety of computer-readable media to facilitate control of the computer 710 to implement one or more aspects of the disclosed subject matter. The computer-readable media can be any available media that can be accessed by the computer 710 and includes volatile and nonvolatile media, and removable and non-removable media. By way of example, and not limitation, computer-readable media may comprise computer storage media and communication media.

Computer storage media includes volatile and nonvolatile, removable and non-removable media implemented in any method or technology for storage of information such as computer-readable instructions, data structures, program modules, or other data. Computer storage media includes, but is not limited to memory devices (e.g., random access memory, read-only memory, electrically erasable programmable read-only memory, et cetera), magnetic storage devices (e.g., hard disk, floppy disk, cassettes, tape, et cetera), optical disks (e.g., compact disk, digital versatile disk, et cetera), and solid state devices (e.g., solid state drive, flash memory drive such as a card, stick, or key drive, et cetera), or any other medium which can be used to store the desired information and which can be accessed by the computer 710.

Communication media typically embodies computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Also, a connection can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above can also be included within the scope of computer-readable media.

Memory 730 and mass storage 750 are examples of computer-readable storage media. Depending on the exact configuration and type of computing device, memory 730 may be volatile (e.g., RAM), non-volatile (e.g., ROM, flash memory, et cetera) or some combination of the two. By way of example, the basic input/output system (BIOS), including basic routines to transfer information between elements within the computer 710, such as during start-up, can be stored in nonvolatile memory, while volatile memory can act as external cache memory to facilitate processing by the processor(s) 720, among other things.

Mass storage 750 includes removable/non-removable, volatile/non-volatile computer storage media for storage of large amounts of data relative to the memory 730. For example, mass storage 750 includes, but is not limited to, one or more devices such as a magnetic or optical disk drive, floppy disk drive, flash memory, solid-state drive, or memory stick.

Memory 730 and mass storage 750 can include, or have stored therein, operating system 760, one or more applications 762, one or more program modules 764, and data 766. The operating system 760 acts to control and allocate resources of the computer 710. Applications 762 include one or both of system and application software and can exploit management of resources by the operating system 760 through program modules 764 and data 766 stored in memory 730 and/or mass storage 750 to perform one or more actions. Accordingly, applications 762 can turn a general-purpose computer 710 into a specialized machine in accordance with the logic provided thereby.

All or portions of the claimed subject matter can be implemented using standard programming and/or engineering techniques to produce software, firmware, hardware, or any combination thereof to control a computer to realize the disclosed functionality. By way of example and not limitation, social identity server 490 (or portions thereof) and/or an instance of service(s) 318 (or portions thereof) can be, or form part, of an application 362, and include one or more modules 764 and data 766 stored in memory and/or mass storage 750 whose functionality can be realized when executed by one or more processor(s) 720.

In accordance with one particular embodiment, the processor(s) 720 can correspond to a system on a chip (SOC) or like architecture including, or in other words integrating, both hardware and software on a single integrated circuit substrate. Here, the processor(s) 720 can include one or more processors as well as memory at least similar to processor(s) 720 and memory 730, among other things. Conventional processors include a minimal amount of hardware and software and rely extensively on external hardware and software. By contrast, an SOC implementation of processor is more powerful, as it embeds hardware and software therein that enable particular functionality with minimal or no reliance on external hardware and software. For example, the social identity server 490 (and/or associated functionality) and/or service(s) 318 (and/or associated functionality) can be embedded within hardware in a SOC architecture.

The computer 710 also includes one or more interface components 770 that are communicatively coupled to the system bus 740 and facilitate interaction with the computer 710. By way of example, the interface component 770 can be a port (e.g., serial, parallel, PCMCIA, USB, FireWire, et cetera) or an interface card (e.g., sound, video, et cetera) or the like. In one example implementation, the interface component 770 can be embodied as a user input/output interface to enable a user to enter commands and information into the computer 710 through one or more input devices (e.g., pointing device such as a mouse, trackball, stylus, touch pad, keyboard, microphone, joystick, game pad, satellite dish, scanner, camera, other computer, et cetera). In another example implementation, the interface component 770 can be embodied as an output peripheral interface to supply output to displays (e.g., CRT, LCD, plasma, et cetera), speakers, printers, and/or other computers, among other things. Still further yet, the interface component 770 can be embodied as a network interface to enable communication with other computing devices, such as over a wired or wireless communications link.

In view of the example, devices and elements described herein, or independent thereof, methodologies that may be implemented in accordance with the disclosed subject matter will be better appreciated with reference to the flow charts. While for purposes of simplicity of explanation, the methodologies are shown and described as a series of block steps, the claimed subject matter is not limited by the order of the block steps, as some block steps may occur in different orders and/or concurrently with other block steps from what is depicted and described herein. Moreover, not all illustrated block steps may be required to implement the methods described herein, or other steps or aspects finding support elsewhere in the specification may be invoked without being expressly illustrated.

Figure 8:
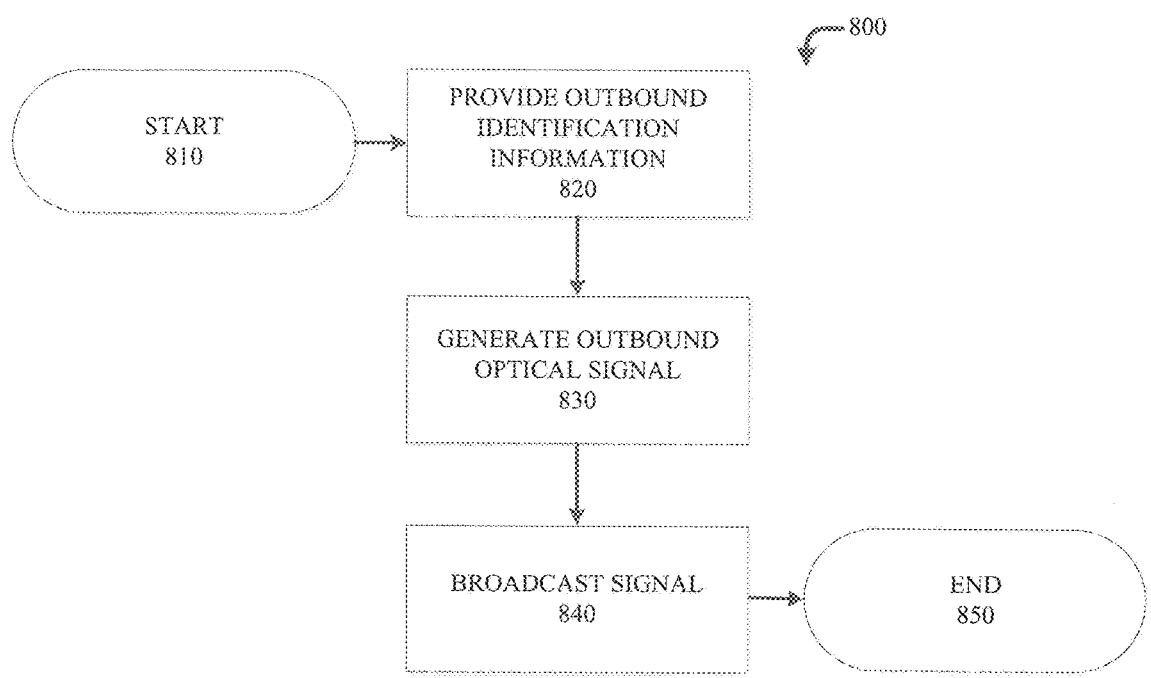
FIG. 8 is an illustration of a flow chart of a methodology for sending optical signals from a portable social client.

FIG. 8 is an illustration of a flow chart of a methodology 800 for sending optical signals from a portable social client. Methodology 800 begins at 810 and proceeds to 820 where outbound identification information is provided. Outbound identification information can be sourced from local or remote memory, or received by other techniques (e.g., data is created through manual input or sensor locally or remotely).

At 830, an outbound optical signal is generated based at least in part on the outbound identification information. In embodiments, the outbound optical signal encodes the outbound identification information into an optical signal format. Alternatively, a portion of the outbound identification information is encoded with other portions of the outbound identification information available through another client-to-client communication (e.g., Wi-Fi, Bluetooth) and/or server-to-client communication. In still another alternative, the outbound optical signal provides an encoded link or instructions for accessing the outbound identity information through a client-to-client communication or from a remote server.

At 840, the outbound optical signal is broadcast. Broadcasting the signal can be completed using visible and/or invisible spectrum light pulses, which aggregate to a pattern or code, which the signal represents and from which data can be discerned. The signal can be broadcast continuously, periodically, or on-demand.

Figure 9:
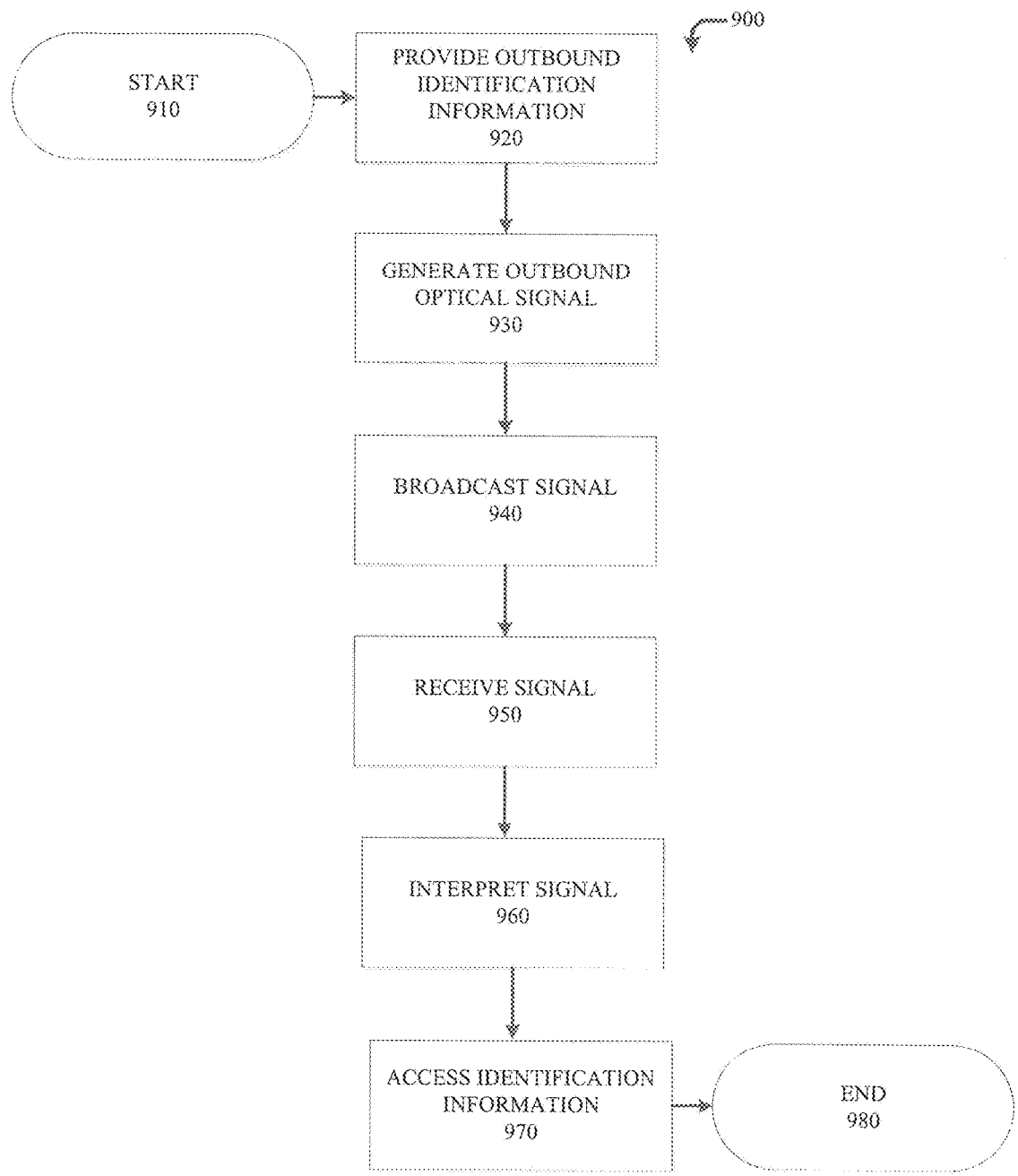
FIG. 9 is an illustration of a flow chart of a methodology for sending and receiving optical signals from a portable social client.

FIG. 9 is an illustration of a flow chart of a methodology 900 for sending and receiving optical signals from a portable social client. Methodology 900 begins at 910 and proceeds to 920 where outbound identification information is provided. At 930, an outbound optical signal is generated based at least in part on the outbound identification information. The outbound optical signal is broadcast at 940.

At 950, the optical signal is received by a social client distinct from the broadcasting social client (e.g., associated with or worn by another user). At 960, the optical signal is interpreted by the receiving social client. Interpretation can include, but is not limited to, decoding a signal to discern underlying information (e.g., at least a portion of identification information), communicating with the transmitting social client directly to exchange information, and/or communicating with a server to exchange information. Based on this interpretation, the identification information associated with the optical signal is accessed at 970. After accessing the identification information associated with the optical signal at 970, methodology 900 ends at 980.

Figure 10:
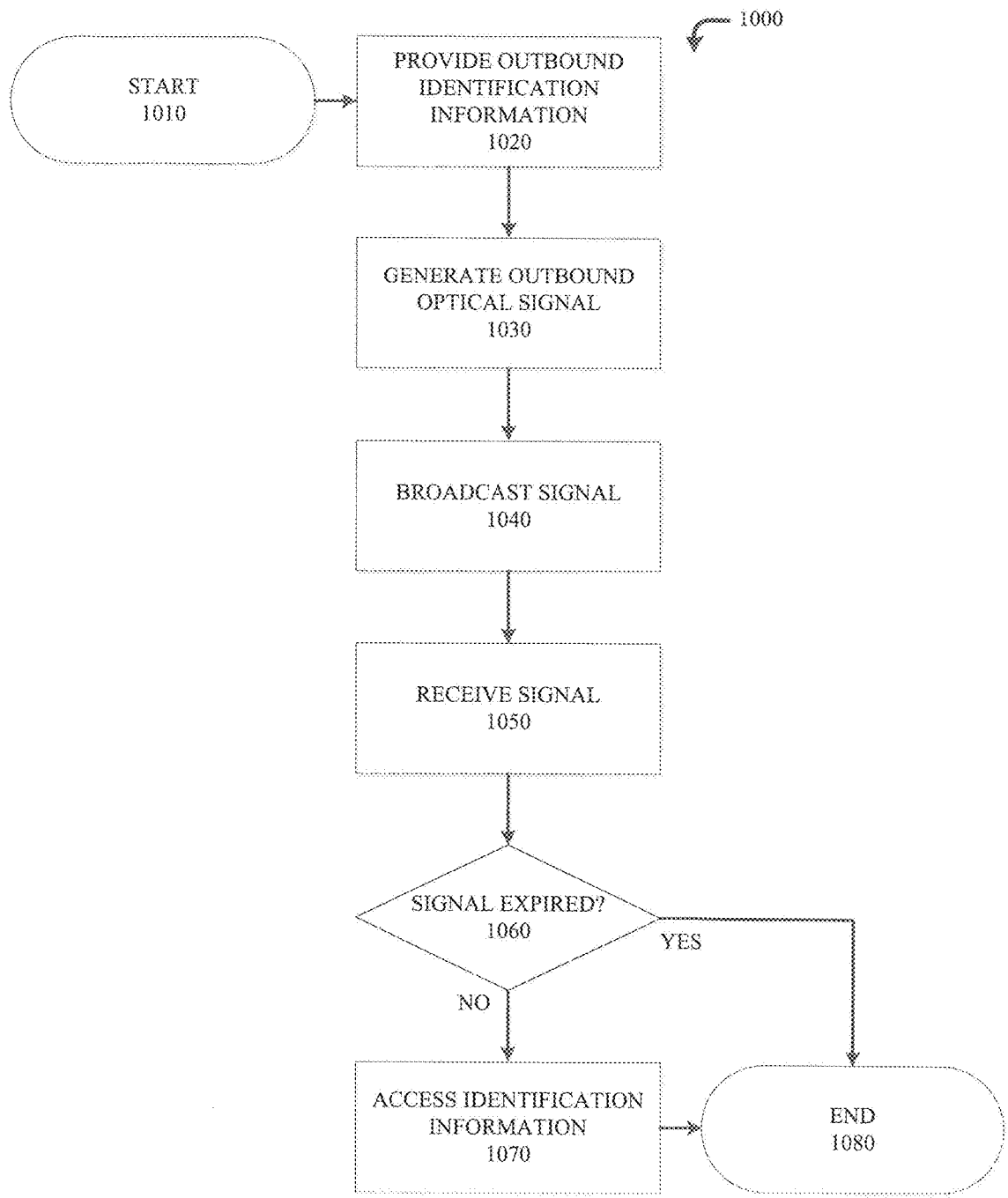
FIG. 10 is an illustration of a flow chart of another methodology for sending and receiving signals from a portable social client.

FIG. 10 is an illustration of a flow chart of another methodology 1000 for sending and receiving signals from a portable social client. Methodology 1000 starts at 1010 and proceeds to 1020 where outbound identification information is provided. At 1030, an outbound optical signal is generated based at least in part on the outbound identification information. The outbound optical signal is broadcast at 1040.

At 1050, a social client distinct from the broadcasting social client receives (e.g., encounters and attempts to interpret) the optical signal. However, before identification information can be accessed, a determination is made at 1060 as to whether the signal is expired. While the determination at 1060 focuses on whether the signal has passed its expiration period, other determinations can be made as well to determine whether access is proper. For example, an evaluation of transmitter and receiver locations, whether a handshake or negotiation has been completed using a non-optical signal communication means, whether the signal exposure was appropriate, whether users associated with a transmitter or receiver have appropriate permissions, et cetera, can be completed similar to an assessment of expiration at 1060. If the signal is expired, or other conditions are not met, methodology 1060 proceeds to end at 1080 without accessing the identification information.

If the signal is not expired, or provided other conditions are met (e.g. negotiation successful), methodology 1000 proceeds to 1070 where identification information is accessed by the receiving social client (e.g., through decoding, interpreting, executing, or subsequent communication with the transmitting social client or an intermediary server). Thereafter, methodology 1000 advances to 1080 where methodology 1000 ends.

Various existing technologies can be leveraged in the implementation of some embodiments herein. For example, Adafruit FLORA devices can be used with some embodiments herein. In another example, Sparkfun Lilypad devices can be used with some embodiments herein. In another example, Arduino devices can be used with some embodiments herein. In another example, Digi devices can be used with some embodiments herein. In another example, Microsoft .net or similar environments can be used with some embodiments herein. While the listing of these technologies is provided for purposes of example and to provide an indication of some technologies compatible in particular embodiments, it is in no way intended to be construed as exhaustive, exclusive, or limiting. Those skilled in the art will appreciate various technologies appropriate for use in alternative or complementary embodiments.

In embodiments, third-party techniques or integrations can be employed (e.g., Google® Project Glass). For example, systems or methods herein can integrate with the third-party embodiments. In other embodiments, systems and methods herein can "outsource" to the third party, using the third party's hardware, or using non-third-party hardware but transmitting information to the third party for processing. In other embodiments, all aspects are wholly contained within systems and methods herein.

While principles and modes of operation have been explained and illustrated with regard to particular embodiments, it must be understood, however, that this may be practiced otherwise than as specifically explained and illustrated without departing from its spirit or scope. For example, while specific placements, configurations, and orientations are shown and described herein, it is to be understood that alternative embodiments can include alternative placements, configurations, and orientations. These alternatives are to be included within the scope of the specification herein. Also, it is to be appreciated that various substitutions in terms of data or media can facilitate similar function. For example, where audio is described, it is to be appreciated that video, audio or combination thereof can be employed in alternative embodiments. Embodiments are intended to embrace all such alterations, modifications, and variations that fall within the spirit and scope of the description. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system, comprising:
    a portable social client including:
        a memory configured to store at least outbound identity information related to a user of the portable social client;
        an encoder configured to associate at least the outbound identity information from the memory with an outbound optical signal pattern;
        an optical signal transmitter configured to broadcast the outbound optical signal pattern;
        an optical signal receiver of the portable social client, the optical signal receiver is configured to receive an inbound optical signal pattern;
    a decoder of the portable social client, the decoder is configured to access inbound identity information associated with the inbound optical signal pattern to identify a user associated with the inbound optical signal pattern; and
        a location module configured to determine a location of the portable social client;
    wherein the portable social client is wearable,
    wherein at least one of the inbound optical signal pattern and the outbound optical signal pattern is further associated with an expiration time after which at least a portion of the inbound identity information or the outbound identity information is inaccessible by way of the decoder and the inbound optical signal pattern or the outbound signal pattern; and
    wherein the outbound optical signal pattern is based at least in part on the location of the portable social client.

2. The system of claim 1, further comprising:
    a wireless communication transceiver of the portable social client.

3. The system of claim 2, wherein the wireless communication transceiver is configured to communicate with at least a social identity server hosting at least the outbound identity information.

4. The system of claim 2, wherein the encoder associates the outbound identity information from the memory with the outbound optical signal pattern by creating the outbound optical signal pattern linking to the outbound identity information on a social identity server.

5. The system of claim 2, wherein the encoder associates the outbound identity information from the memory with the outbound optical signal pattern by partially encoding the outbound identity information from the memory into the outbound optical signal pattern and linking a remainder of the outbound identity information from the memory to the information on a social identity server.

6. The system of claim 2, wherein interpretation of the outbound optical signal pattern by a remote device facilitates access to the outbound identity information, and wherein the wireless communication transceiver transmits the outbound identity information.

7. The system of claim 1, wherein the encoder associates the outbound identity information from the memory with the outbound optical signal pattern by encoding the outbound identity information from the memory in the outbound optical signal pattern.

8. The system of claim 1, further comprising:
    the optical signal receiver of the portable social client, the optical signal receiver is configured to receive the inbound optical signal pattern; and
    the decoder of the portable social client, the decoder is configured to interpret the inbound optical signal pattern, wherein interpretation of the inbound optical signal pattern permits access inbound identity information associated with the inbound optical signal pattern,
    wherein the inbound optical signal pattern is interpreted based at least in part on the location of the portable social client.

9. The system of claim 1, wherein the optical signal transmitter broadcasts in one of ultra-violet light and infrared light.

10. The system of claim 1, wherein the optical signal transmitter broadcasts in color light.

* * * * *